United States Patent
Albano et al.

(10) Patent No.: US 6,469,180 B1
(45) Date of Patent: Oct. 22, 2002

(54) AMORPHOUS FORM OF CELL INHIBITOR HAVING IMPROVED SOLUBILITY AND BIOAVAILABILITY

(75) Inventors: Antonio A. Albano; Wantanee Phuapradit, both of Clifton; Harpreet K. Sandhu, West Orange; Navnit Hargovindas Shah, Clifton, all of NJ (US)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 10/120,463

(22) Filed: Apr. 11, 2002

Related U.S. Application Data (62) Division of application No. 09/928,635, filed on Aug. 13, 2001
(60) Provisional application No. 60/237,563, filed on Oct. 3, 2000.

(51) Int. Cl.$^7$ ............................................. C07D 403/14
(52) U.S. Cl. ..................................................... 548/455
(58) Field of Search ........................................ 548/455

(56) References Cited

U.S. PATENT DOCUMENTS 5,057,614 A * 10/1991 Davis et al. ............... 548/466
6,048,887 A    4/2000  Dhingra et al.
6,036,736 A    6/2000  Davis et al.
6,326,501 B1  12/2001  Jiang
6,350,786 B1   2/2002  Albano et al.

FOREIGN PATENT DOCUMENTS

EP          0 988 869          3/2000

* cited by examiner

Primary Examiner—Joseph K. McKane
Assistant Examiner—Rebecca Anderson
(74) Attorney, Agent, or Firm—George W. Johnston; Patricia S. Rocha-Tramaloni

(57) ABSTRACT

The present invention provides a method for preparing an amorphous, pharmaceutically active form of a compound of formula I

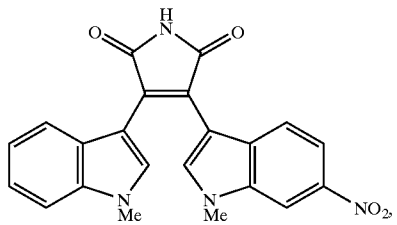

which is substantially free of crystalline compound.

3 Claims, 6 Drawing Sheets

POWDER X-RAY DIFFRACTION PATTERN OF COMPOUND OF FORMULA I PREPARED IN ACCORDANCE WITH INVENTION

AMORPHOUS FORM OF CELL INHIBITOR HAVING IMPROVED SOLUBILITY AND BIOAVAILABILITY

This application is a divisional of Ser. No. 09/928,635, filed Aug. 13, 2001 now allowed and claims priority to prior provisional application Serial No. 60/237,563, filed on Oct. 3, 2000 claimed under 35 U.S.C. §119(e).

SUMMARY OF THE INVENTION

The present invention provides an amorphous, pharmaceutically active form of a compound of formula I which is substantially free of crystalline compound. This compound is also known as 3-(1-methyl-3-indolyl)-4-(1-methyl-6-nitro-3-indolyl)-1H-pyrrole-2,5,-dione. This invention also provides a process for making the, amorphous form of the compound of formula I as well as pharmaceutical compositions including such compound.

BACKGROUND OF THE INVENTION

A crystalline form of the compound of formula I is known. See, e.g., U.S. Pat. No. Re. 36,736. This crystalline form has a melting point of approximately 285° C. (Id. column 22, lines 5–6). This compound belongs to a novel class of cell cycle inhibitors and apoptosis-inducers having potent anti-cancer therapeutic activity, in particular in solid tumors such as non-small cell lung, breast and colorectal cancers. See, e.g. U.S. Pat. No. 6,048,887 and EP 0 988,863. In its previously known crystalline form, compound of formula I has relatively low aqueous solubility (<10 µg/mL) at physiological pHs (which range from 1.5–8.0) and consequently less than optimal bioavailability (less than 5% in dogs). As this is a therapeutically active compound, it is thus desirable to obtain a form of the compound of formula I which has improved solubility/dissolution rate and bioavailability.

The bioavailability of a therapeutically active compound is generally determined by (i) the solubility/dissolution rate of the compound, and (ii) the partition coefficient/permeability of the compound through a subject's gastrointestinal membrane. The major cause of poor bioavailability of a therapeutically active compound is usually the poor solubility/dissolution rate of said compound. Poor bioavailability is also often accompanied by high variable patient blood levels and unpredictable dose/therapeutic effects due to erratic absorption of the drug by the patient.

Several techniques can be used to improve the bioavailability of therapeutically active compounds having relatively low aqueous solubility. These techniques are discussed in the background Section of EP 0988,863. Also described in EP 0988,863, is a novel process pursuant to which crystalline therapeutically active compounds having relatively low aqueous solubilities may be rendered more bioavailable by being incorporated or dispersed in an ionic polymer.

While the dispersion or incorporation of therapeutically active compounds having relatively low aqueous solubilities in ionic polymers using certain methods may increase the bioavailability of these compounds, these methods can be cumbersome and time consuming. Such methods also require that the therapeutically active compounds are delivered to a patient in combination with a polymer, which may not always be beneficial or desirable. It is thus desirable to develop a process of making the compound of formula I in its amorphous form which does not require dispersion of the compound in a polymer.

SUMMARY OF THE INVENTION

The invention relates to an amorphous form of the compound of formula I which is substantially free of the crystalline form of the compound. This amorphous (also referred to as "high energy") form of the compound of formula I exhibits a faster dissolution rate than and superior bioavailability to the previously known crystalline form of the compound. The bioavailability of the amorphous form of the compound of this invention is significantly higher than the crystalline form of the compound, thereby enabling the amorphous form of the compound to be used in the treatment or therapy of cancerous tumors.

Another aspect of the invention relates to stable, amorphous compound of formula I which remains in stable, amorphous form for a period of time to permit the compound to have a reasonable shelf life (for example, two (2) years at room temperature) independent of form stabilizers such as an ionic polymer.

Another aspect of the invention is a process for making the high energy amorphous compound of formula 1.

Another aspect of the invention is a pharmaceutical composition including a therapeutically effective amount of the compound of formula I in amorphous form.

DETAILED DESCRIPTION OF THE INVENTION

The present invention provides a high energy, amorphous, pharmaceutically active form of a compound of formula I As prepared in accordance with the present invention, the amorphous form of the compound of formula I has very high bioavailability (approximately 15-fold higher) as compared to the crystalline form, enabling the compound to be used in a pharmaceutical product. Not only does the amorphous form of the compound exhibit a superior dissolution rate and bioavailability in contrast to the crystalline form, but due to its high glass transition temperature of approximately 112° C., it retains its amorphous properties independent of form stabilizers.

The amorphous form of compound I according to the present invention significantly facilitates the delivery to a patient of a pharmaceutically active compound that in its crystalline form has relatively low aqueous solubility and poor bioavailability.

As used herein, the following terms shall have the following meanings.

"Amorphous Compound" means that the compound does not exhibit a typical endotherm in a differential scanning calorimetry thermogram and does not have distinct peaks in a powder x-ray diffraction pattern. This form of a compound is also referred to as the "high energy" form of the compound.

"Dissolution Rate" means the speed with which a particular compound dissolves in a particular dissolution medium.

"Form Stabilizers" are substances such as ionic polymers which can be used to immobilize a compound in a particular physical form (e.g. amorphous form) thereby protecting the compound from environmental factors (such as for example heat, moisture, etc.).

"Patient" refers to a human subject.

"Relatively Low Aqueous Solubility" means that a particular compound or form thereof has an aqueous solubility of less than about 10 μg/mL.

"Substantially free of crystalline compound" means that the compound is not more than about 20% crystalline form, preferably not more than about 10% crystalline form.

Methods of Preparation of Amorphous Compound of Formula I

The high energy or amorphous form of the compound of formula I may be prepared by the following methods:

Spray Drying or Lyophilization: The compound of formula I, in a crystalline form, is dissolved in an organic solvent. Suitable organic solvents for this process include ethanol, methanol, acetone, dimethyl sulfoxide, N,N-dimethylacetamide, N,N-dimethylformamide, N-methylpyrrolidone, diethylene glycol, ethyl ether, glycofural, propylene carbonate, tetrahydrofuran, polyethylene glycols, and propylene glycols. The solvent is then removed by spray drying or lyophilization, yielding amorphous compound of formula I.

Solvent Controlled Precipitation: In a preferred embodiment of the invention, crystalline compound of formula I is dissolved in an organic solvent. Suitable organic solvents for this process include those listed above in a). The compound is then precipitated, preferably in aqueous solution, and preferably at a pH where the compound is not soluble. The resulting precipitate is amorphous compound of formula I and can be recovered by procedures known to those skilled in the art, such as for example, by filtration, centrifugation and washing, etc. The recovered precipitate is then dried (in air, an oven, or a vacuum) and the resulting solid can be further processed, such as milling, pulverizing or micronizing to a fine powder by means known in the art.

Supercritical Fluid: Crystalline compound of formula I is dissolved in a supercritical fluid such as liquid nitrogen or liquid carbon dioxide (at supercritical temperature and pressure). The supercritical fluid is then removed by evaporation, leaving the precipitated compound in amorphous form. Alternatively, the compound of formula I is dissolved in an organic solvent as described above in a). A supercritical fluid is used as an anti-solvent for extraction of the organic solvent, causing the compound to precipitate in amorphous form from the organic solvent.

Hot Melt Extrusion: Crystalline compound of formula I is fed continuously to a temperature-controlled extruder which is set at different temperature gradients. Specifically, the crystalline compound is extruded and, melted in a hot melt extruder, followed by abruptly cooling to room temperature, which causes the compound to solidify or precipitate in amorphous form. The resulting extrudate can then be milled into a fine powder.

The amorphous form of the compound of formula I prepared according to the present invention can then be combined with appropriate pharmaceutically acceptable excipients to yield a pharmaceutical preparation for administration to patients. These excipients include, but are not limited to, inorganic or organic carriers, fillers, binders, disintegrants, lubricants, preservatives, solubilizing agents, stabilizers, wetting agents, emulsifying agents, sweetening agents, coloring agents, flavoring agents, salts for varying the osmotic pressure, buffers, coating agents, antioxidants, and control release agents, all of which are known in the art.

The resulting products from the above-described methods a)–d) can be further processed by means known in the art for incorporation in a pharmaceutical formulation.

This invention also contemplates pharmaceutical preparations that include a therapeutically effective amount of a compound of formula I in amorphous form. A therapeutically effective amount means an amount, at such dosages and for such periods of time, necessary to achieve the desired therapeutic result. Moreover, such amount must be one in which the overall therapeutically beneficial effects outweigh any toxic or undesirable side effects. A therapeutically effective amount of a compound often varies according to disease state, age and weight of the subject being treated. Thus, dosage regimens are typically adjusted to the individual requirements in each particular case and are within the skill in the art.

The appropriate daily dose of compound I in amorphous form for oral administration to an adult human weighing about 70 kg is from about 100 mg to about 1,500 mg, preferably from about 400 mg to about 800 mg, although: the upper limit may be exceeded when indicated. The daily oral dosage can be administered as a single dose or in divided doses, or for parenteral administration, can be given as a continuous infusion.

This invention also contemplates a process for preparing amorphous compound of formula I without dispersing the compound in an ionic polymer.

The following examples illustrate methods for making the amorphous compound of the present invention as well as pharmaceutical preparations incorporating said amorphous compound. These examples illustrate the present invention and are not intended to be limiting.

EXAMPLES

Example I

General Preparation of Amorphous Compound

Crystalline compound of formula I was dissolved in dimethylacetamide. The resulting solution was then slowly added to cold (2°–10° C.) aqueous solution at pH 2–7. This caused the compound to precipitate as amorphous compound. The precipitate was washed several times with cold (2°–10° C.) water until the residual dimethylacetamide was below 0.3%. The precipitate was dried and milled into the desirable particle size.

Example II

Preparation of Pharmaceutical Preparations Including Amorphous Compound of formula I The powder form of the amorphous compound prepared in accordance with Example I above was then incorporated with various pharmaceutical excipients to yield the following pharmaceutical formulations:

| Formulation | % w/w |
| --- | --- |
| Amorphous Compound of Formula I | 50 |
| Lactose Anhydrous | 50 |

Method of Preparation of Formulation

Amorphous compound of formula I (with a mean particle size of 8 microns as determined by a laser light scattering instrument), which was prepared in accordance with Example I, was mixed with lactose anhydrous in a mixer for 10 minutes.

The resulting powder blend form Step 1 was encapsulated into a capsule.

| Formulation | % w/w |
| --- | --- |
| Amorphous Compound of Formula I | 50 |
| Methocel K100LV | 40 |
| Microcrystalline Cellulose | 7 |
| Talc | 2 |
| Magnesium Stearate | 1 |

Method of Preparation of Formulation

Amorphous compound of formula I (with a mean. particle size of 8 microns as determined by a laser light scattering instrument), which was prepared in accordance with Example I, was mixed with Methocel K100LV (hydroxypropyl methylcellulose; Dow Chemicals, Ml) in a mixer for 10 minutes.

The powder mix from Step 1 was granulated with purified water until a uniform granulation was obtained.

The granulation from Step 2 was dried in an oven at 50° C. until the moisture content was less than 2% as determined by a loss on drying apparatus operating at 90° C.

The dried granulation from Step 3 was milled into a fine powder.

The milled granulation from Step 4 was blended with microcrystalline cellulose, talc and magnesium stearate for 5 minutes.

The powder blend from Step 5 was compressed into a tablet using a tablet press.

| Formulation | % w/w |
| --- | --- |
| Amorphous Compound of Formula I | 50 |
| Corn Starch | 10 |
| Lactose | 39 |
| Talc | 1 |

Method of Preparation of Formulation

Amorphous compound of formula I (with a mean particle size of 8 microns as determined by a laser light scattering instrument), which was prepared in accordance with Example I, was mixed with corn starch, lactose and talc for 10 minutes.

The powder blend from Step 1 was encapsulated into a capsule.

| Formulation | % w/w |
| --- | --- |
| Amorphous Compound of Formula I | 50 |
| Klucel LF | 45 |
| Talcum | 3 |
| Magnesium Stearate | 2 |

Method of Preparation of Formulation

Amorphous compound of formula I (with a mean particle size of 8 microns as determined by a laser light scattering instrument), which was prepared in, accordance with Example I was mixed with Klucel LF (hydroxypropyl cellulose; Hercules Inc., N.J.) in a mixer for 10 minutes.

The powder mix from Step 1 was granulated with purified water until a uniform granulation was obtained.

The granulation from Step 2 was dried in an oven at 50° C. until the moisture content was less than 2% as determined by a loss on drying apparatus operating at 90° C.

The dried granulation from Step 3 was milled into a fine powder.

The milled granulation from Step 4 was blended with talc and magnesium stearate for 5 minutes.

The powder blend from Step 5 was compressed into a tablet using a tablet press.

Example III

Preparation of Pharmaceutical Formulations Including Crystalline Compound of formula I

| Formulation | % w/w |
| --- | --- |
| Crystalline Compound of Formula I | 50 |
| Lactose Anhydrous | 50 |

Method of Preparation of Formulation Crystalline compound of formula I (with a mean particle size of 9 microns as determined by a laser light scattering instrument) prepared in accordance with the methods taught in U.S. Pat. RE 36,736 was mixed with lactose anhydrous in a mixer for 10 minutes.

| Formulation | % w/w |
| --- | --- |
| Crystalline Compound of Formula I (micronized) | 4 |
| Methocel K3 | 4 |
| Purified Water | 92 |

Method of Preparation of Formulation

Methocel K3 (hydroxypropyl methylcellulose; Dow Chemicals, MI) was dispersed in a portion of purified water at a concentration of 20% w/w and mixed well until a uniform dispersion was obtained.

Crystalline compound of formula I (with a mean particle size of 5 microns, and prepared in accordance with the methods taught in U.S. Pat. RE 36,736) was added to the dispersion from Step 1 and mixed well until a uniform suspension was obtained.

The remainder of purified water was added to the suspension from Step 2 and mixed well.

| Formulation | % w/w |
| --- | --- |
| Crystalline Compound of Formula I (nanosized) | 4 |
| Methocel K3 | 4 |
| Purified Water | 92 |

Method of Preparation of Formulation

Methocel K3 (hydroxypropyl methylcellulose; Dow Chemicals, MI) was dispersed in purified water at a concentration of 20% w/w and mixed well until a uniform dispersion was obtained.

Crystalline compound of formula I (with a mean particle size of 5 microns and prepared in accordance with the methods taught in U.S. Pat. RE 36,736) was added to the dispersion from Step 1 and mixed well until a uniform suspension was obtained.

The suspension from Step 2 was passed through a DYNOMIL containing glass beads (with mean diameter of 0.2–0.5 mm) as a grinding medium to achieve a mean particle size of compound of formula I in the range of 300–400 nm.

Example IV

Comparison of Physical Properties of Amorphous and Crystalline Compound of Formula I Various tests were conducted to compare crystalline compound of formula I prepared in accordance with the methods taught in U.S. Pat. RE 36,736 with amorphous compound of formula I according to the present invention. Parameters compared include crystallinity, glass transition temperature, dissolution rate and bioavailability. The results of the comparisons are described below and depicted in the accompanying Figures.

Figure 1:
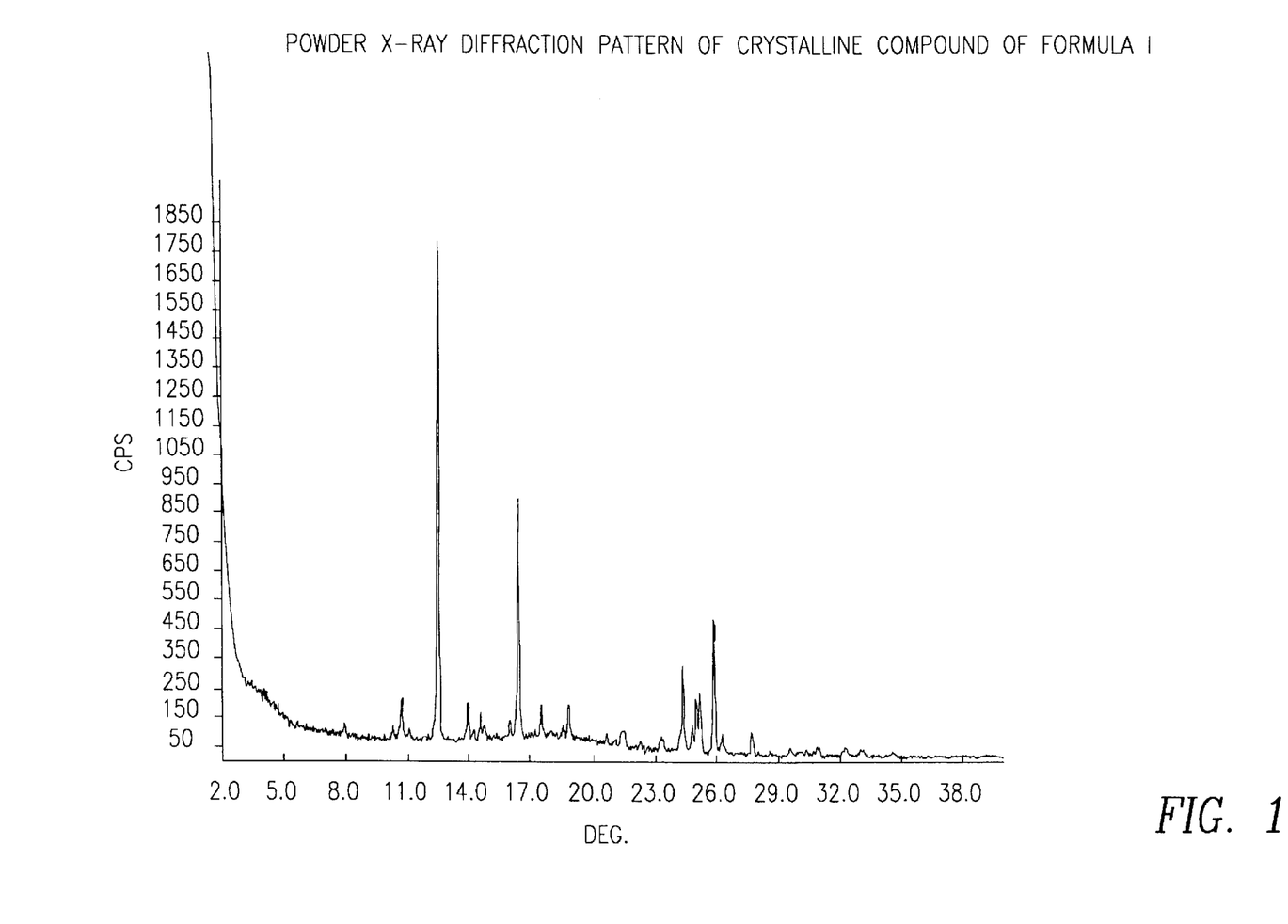
FIG. 1 is a powder x-ray diffraction pattern of compound of formula I prepared according to previously known methods showing the distinct crystallinity of the compound.

As shown in the powder X-ray diffraction pattern in FIG. 1, compound of formula I prepared in accordance with the methods taught in U.S. Pat. RE 36,736 exhibited distinct crystallinity.

Figure 2:
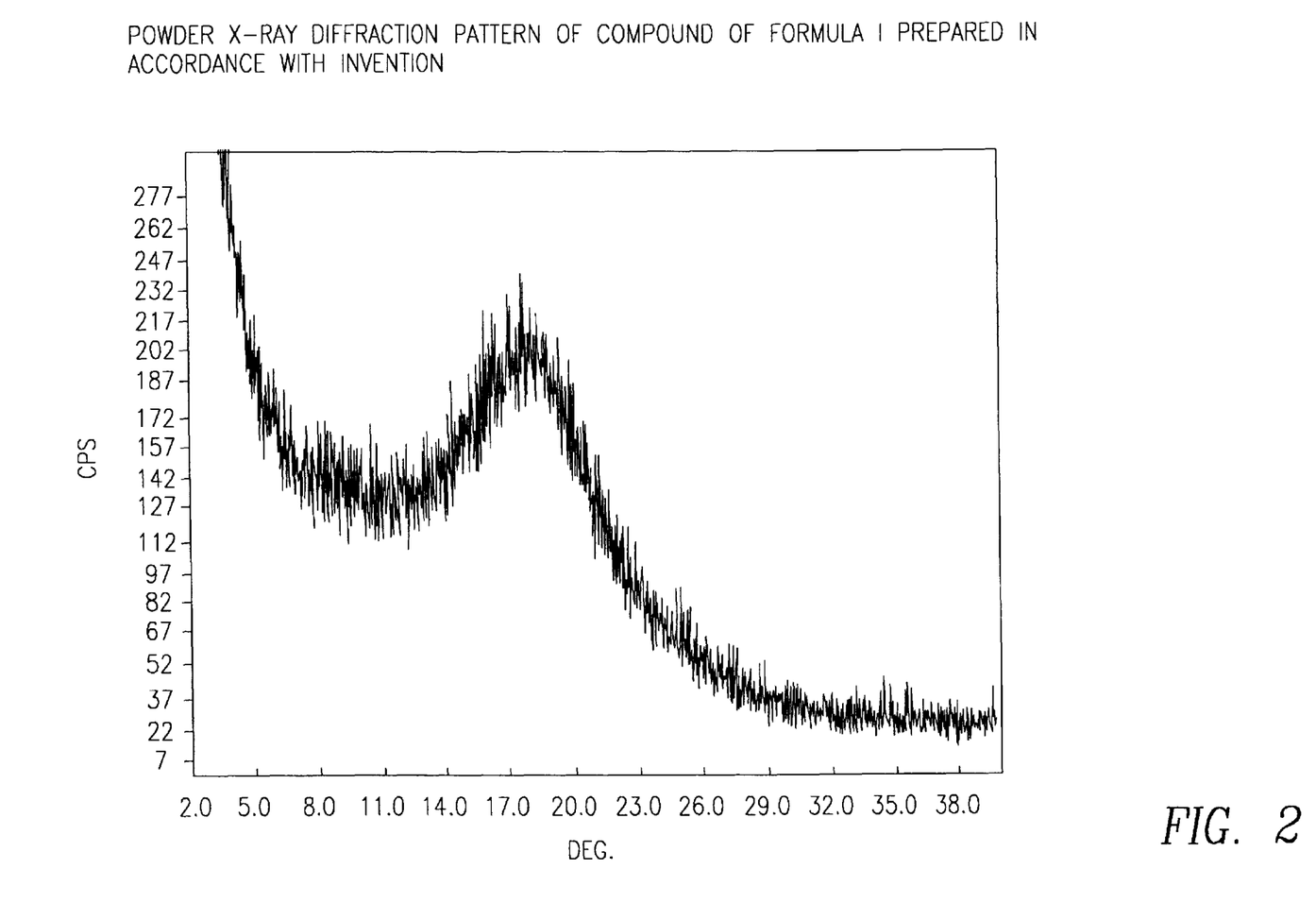
FIG. 2 is a powder x-ray diffraction pattern of compound of formula I prepared in accordance with this invention showing the amorphous characteristics of the compound.

As shown by the powder X-ray diffraction pattern in FIG. 2, compound of formula I which is prepared by the methods taught herein, is distinctly amorphous.

Figure 3:
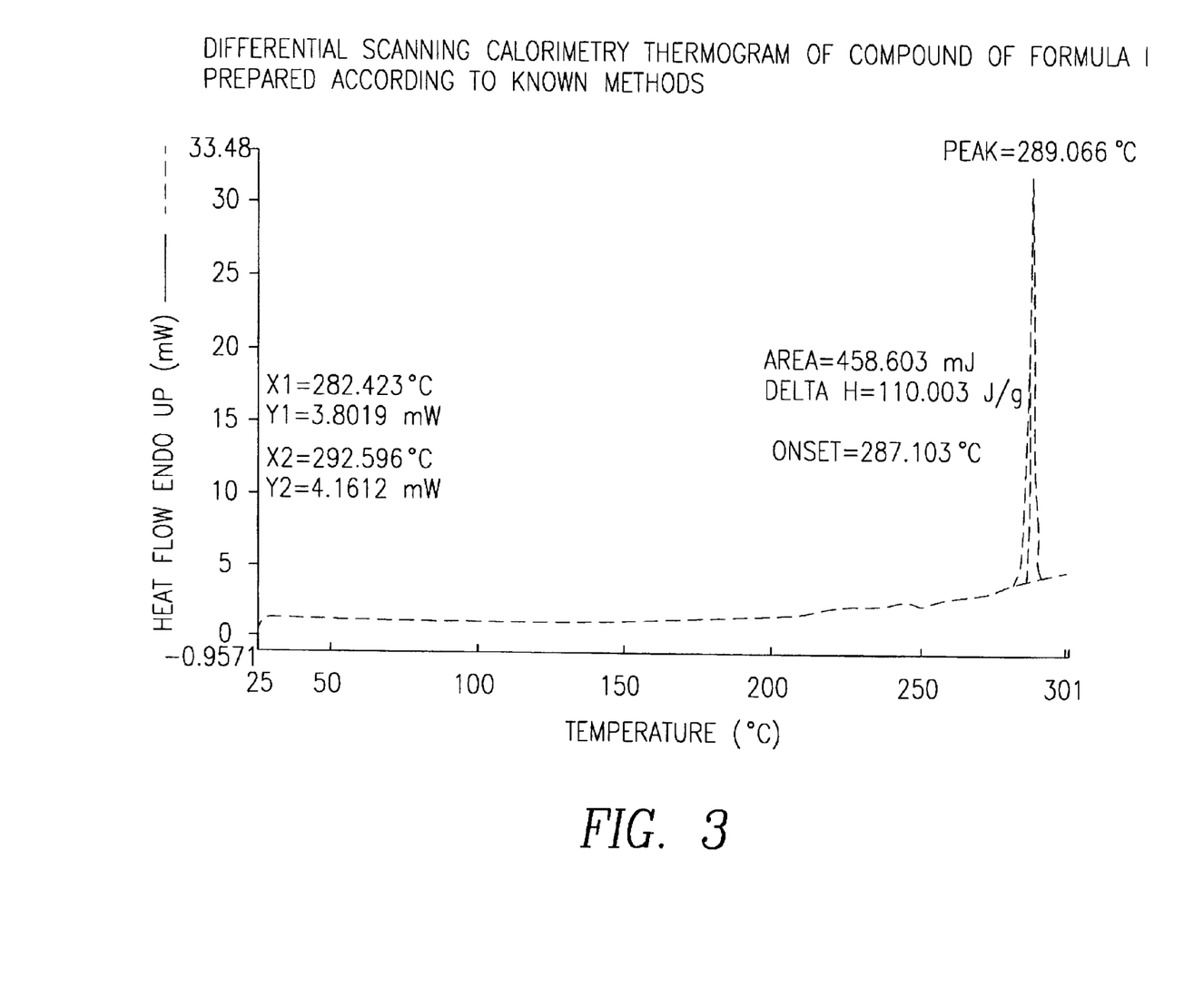
FIG. 3 is a differential scanning calorimetry thermogram of compound of formula I prepared according to previously known methods showing a distinct endotherm for the compound thus evidencing that the compound is in crystalline form.

As shown by a differential scanning calorimetry thermogram in FIG. 3, compound of formula I prepared in accordance with the methods taught in U.S. Pat. RE 36,736 has a distinct endotherm at a temperature of 287° C. and is thus crystalline.

Figure 4:
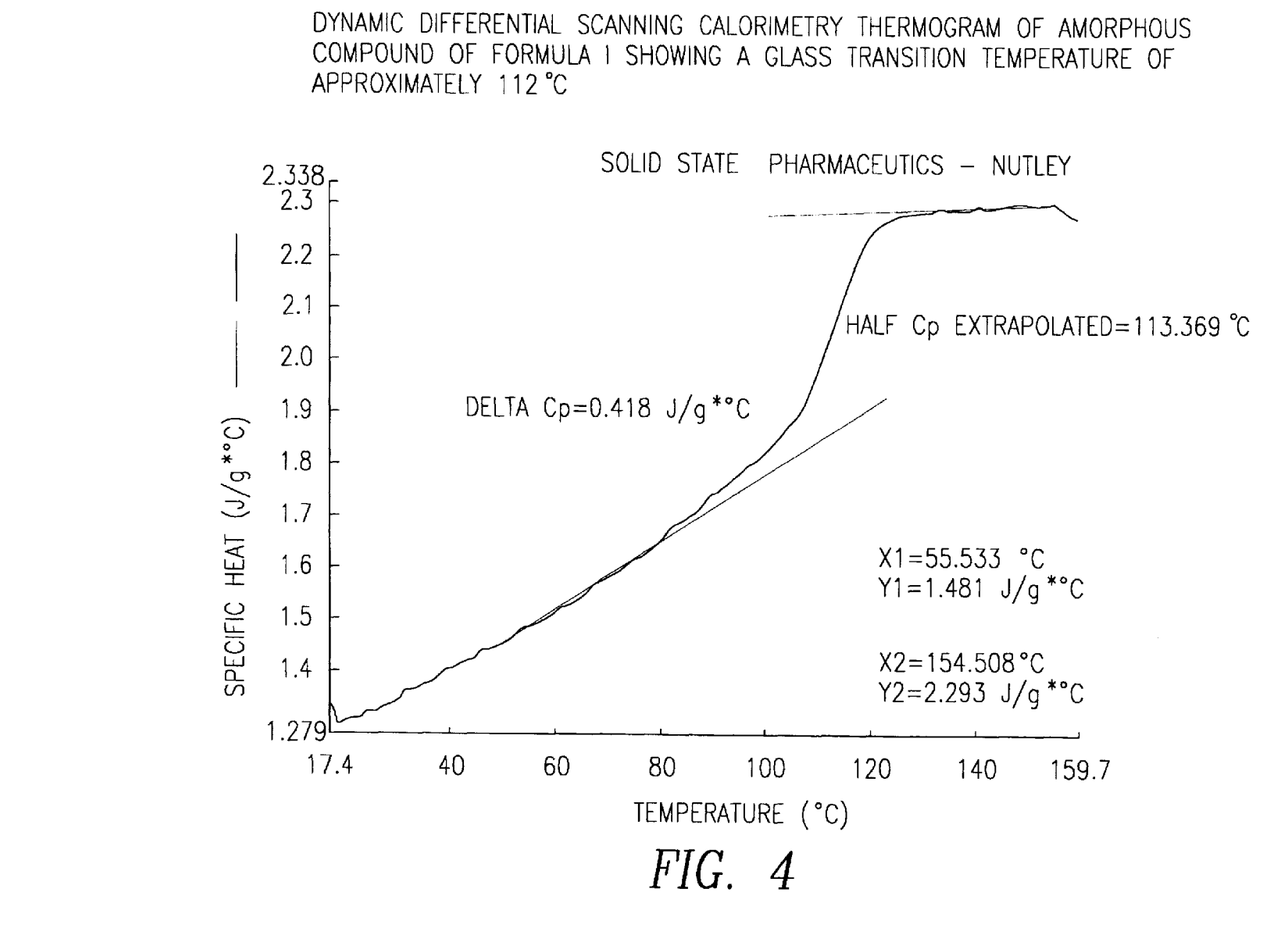
FIG. 4 is a differential scanning calorimetry thermogram of the compound of formula I prepared in accordance with this invention showing a glass transition temperature of approximately 112° C. thus evidencing that the compound is in amorphous form.

As shown by a differential scanning calorimetry thermogram in FIG. 4, compound of formula I prepared in accordance with the methods taught herein has a glass transition temperature of approximately 112° C. and is thus amorphous.

Figure 5:
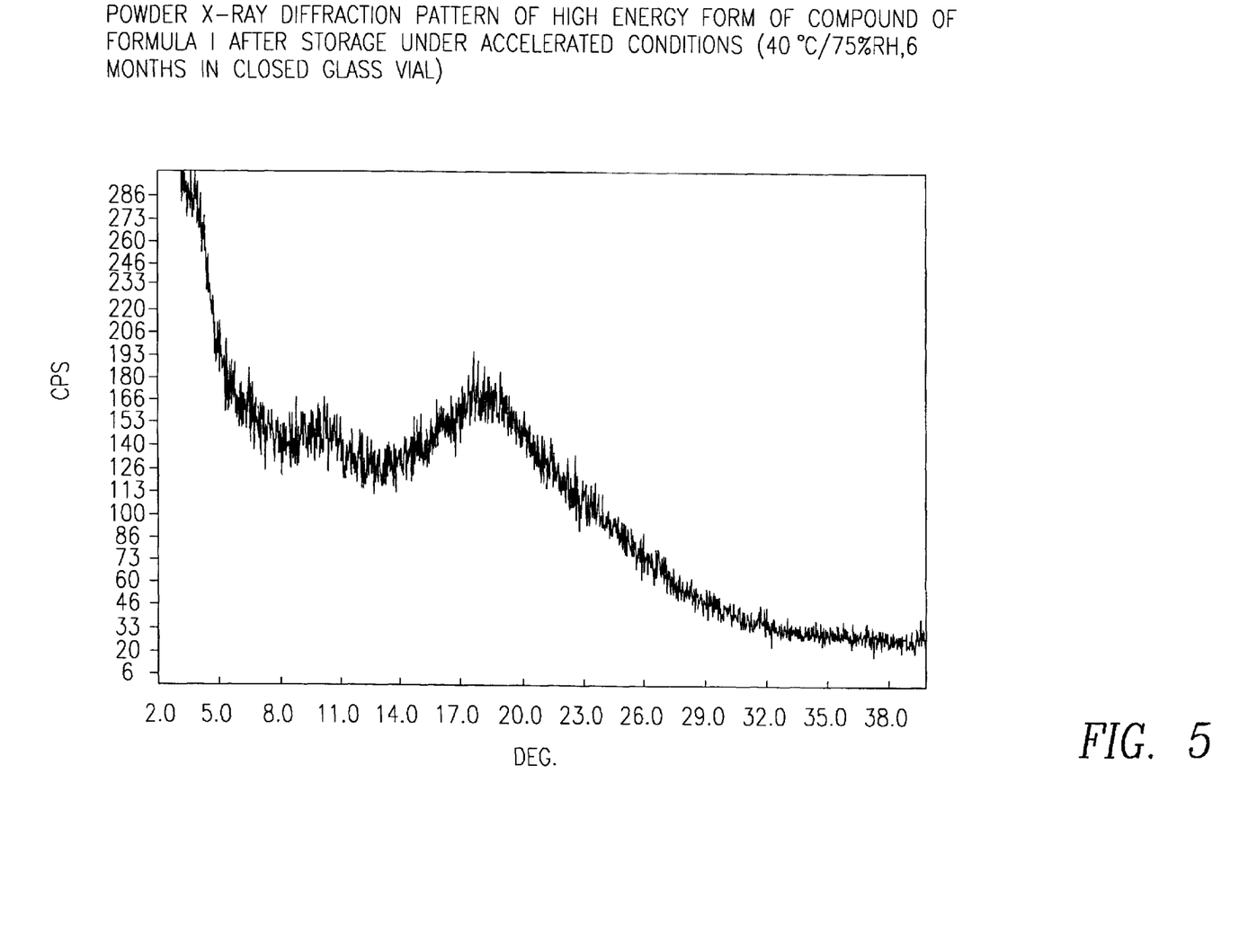
FIG. 5 is a powder x-ray diffraction pattern of compound of formula I prepared in accordance with this invention showing that the compound remained in its amorphous form independent of form stabilizers even when exposed to accelerated storage conditions (40° C./75%RH, closed glass vial for 6 months).

As shown by the powder X-ray diffraction pattern in FIG. 5, amorphous compound of formula I prepared in accordance with the methods taught herein maintained its amorphous properties even under accelerated storage conditions. This means that the compound prepared in accordance with this invention is stable and suitable for incorporation in pharmaceutical formulations.

The formulation of Example IIIA containing crystalline compound of formula I (Example III A) and the formulation of (Example II A) containing amorphous compound of formula I were evaluated for dissolution by a two-stage (two dissolution media) dissolution method. At Stage I, 300 mL of deionized water at 37°±0.5° C. using paddles at 75 rpm was used. At Stage II, 600 mL of 6% w/v Sodium Lauryl Sulfate in 0.015M Phosphate Buffer, pH 6.8 equilibrated at 37°±0.5° C., was carefully added into the dissolution vessel 25 minutes after the Stage I dissolution was initiated. Sample aliquots were taken at different time intervals and analyzed by UV spectrophotometry.

Figure 6:
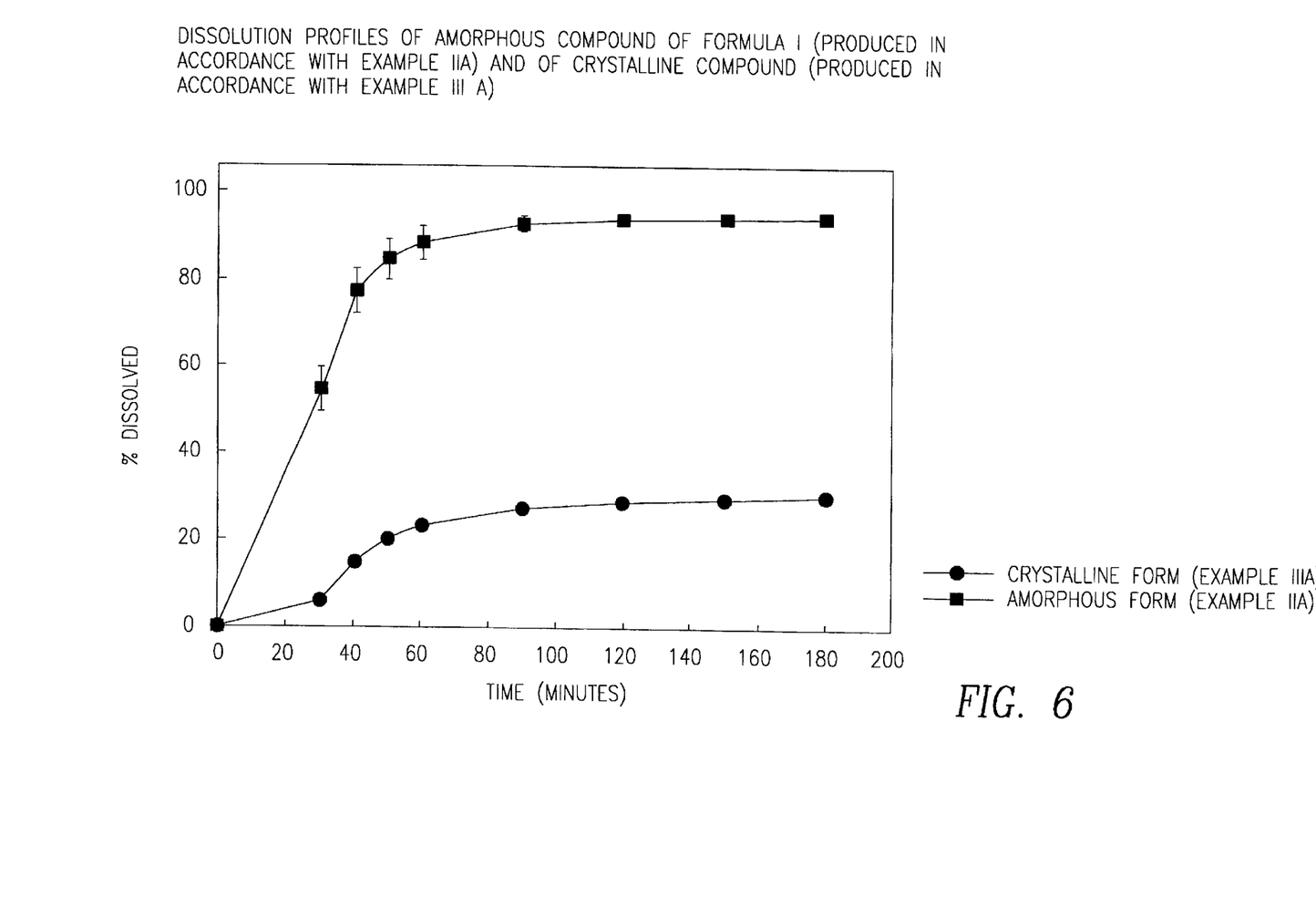
FIG. 6 is the dissolution profile of preparations containing compound of formula I produced in accordance with previously known methods (Example III A) and produced in accordance with this invention (Example II A). This figure shows that the compound of the present invention (amorphous form) is much more soluble than the crystalline form of the compound that was previously available.

As shown in FIG. 6, the results of the above dissolution evaluation clearly indicate that the dissolution profile of the preparation containing amorphous compound of formula I (Example II A) was faster and more complete than that of the preparation containing crystalline compound of formula I (Example III A).

Additionally, preparations containing crystalline compound of formula I (Examples III B and III C) and amorphous compound of formula I (Example II A) were evaluated for bioavailability in beagle dogs with body weight of approximately 10 kg. Each dog was given a formulation containing 90 mg of compound of formula 1. Blood samples were collected from each dog prior to dosing (0 h) and at 0.5, 1, 2, 4, 6, 8, 12, 24, 36 and 48 hours after dosing. EDTA was used as an anticoagulant. Each plasma sample was separated after cold centrifugation and frozen in an amber vial at a minimum of -60° C. before analysis. Compound of formula I was extracted from plasma and the plasma concentration of compound of formula I was determined using a positive ion TurbolonSpray LC-MS/MS assay[HPLC using HP1100 LC system, Hewlett-Packard, Inc. (Agilent Technologies, Wilmington, Del.) and Mass Spectrometer using PE-Sciex API-3+ (Perkin-Elmer Instruments, Wilton, Conn.), Ionization mode: Turbulonspray, 500C, positive ion] The calibration range was 1 to 1,000 ng/mL using a 100-μL plasma sample.

Non-compartmental pharmacokinetic parameters estimated were the maximum plasma concentration (Cmax), the time to reach the Cmax (Tmax), the area under the plasma concentration-time curve ($AUC_{0-\infty}$) from time zero to infinity, dose (mg/kg) normalized Cmax (Cmax/dose) and dose normalized AUC (AUC/dose) for compound of formula I. The observed Cmax and Tmax were taken directly from the concentration-time profile for the individual animal. The $AUC_{0-\infty}$) was calculated using the linear trapezoidal rule by WinNonline™ (Professional Edition version 1.5, Pharsight Corporation, Mountain View, Calif.).

The results of this bioavailability evaluation are given in Table I below. The data reported in Table I show that the bioavailability in dogs of the compound of formula I in amorphous form (Example IIA) is significantly higher than when the crystalline form of the compound (Examples IIIB and IIIC) is administered to the animals in conventional dosage forms (such as micronized and nanosized suspensions).

TABLE I

Pharmacokinetics of Compound of Formula I in Dogs[1] after Single Oral Dose Administration (10 mg/kg)

| Formulation | $AUC_{0-\infty}$/Dose (ng · h/ml)/ (mg/kg) | $T_{max}$ (hr) | $C_{max}$ (ng/ml) | % Bioavailability[2] |
|---|---|---|---|---|
| Micronized crystalline compound I suspension (Example IIIB) | 29.5 ± 8.3 | 1.0 ± 0.0 | 55 ± 17 | 4 |
| Nanosized, crystalline compound I suspension (Example IIIC) | 86.1 ± 13.7 | 1.5 ± 0.6 | 142 ± 53 | 11 |
| Amorphous compound + Lactose Anhydrous (Example IIA)) | 468 ± 87 | 3.4 ± 1.9 | 874 ± 452 | 61 |
| IV Formulation | 766 ± 82 | N/A[3] | N/A[3] | 100 |

N = 4, 2 males and 2 females with a parallel design
When compared to the IV formulation
Not available While the compositions and methods of this invention have been described in terms of preferred embodiments, it will be apparent to those skilled in the art that variations may be made without departing from the concept, spirit and scope of the invention.

We claim:

1. A method of making a compound of formula I in amorphous form substantially free of crystalline compound and not dispersed in an ionic polymer comprising:

(a) dissolving a crystalline compound of formula I in a supercritical fluid; and (b) removing the supercritical fluid.

2. The method of claim 1 wherein the supercritical fluid is liquid nitrogen or liquid carbon dioxide.

3. The method of claim 2 wherein the supercritical fluid is removed by evaporation.

* * * * *

UNITED STATES PATENT AND TRADEMARK OFFICE
CERTIFICATE OF CORRECTION

PATENT NO. : 6,469,180 B1
DATED : October 22, 2002
INVENTOR(S) : Antonio A. Albano et al.

It is certified that error appears in the above-identified patent and that said Letters Patent is hereby corrected as shown below:

<u>Title page,</u>
Item [54], The Title reads: "AMORPHOUS FORM OF CELL INHIBITOR HAVING IMPROVED SOLUBILITY AND BIOAVAILABILITY". The Title should read -- AMORPHOUS FORM OF CELL CYCLE INHIBITOR HAVING IMPROVED SOLUBILITY AND BIOAVAILABILITY --.

Signed and Sealed this

Eighteenth Day of March, 2003

JAMES E. ROGAN
*Director of the United States Patent and Trademark Office*